United States Patent [19]

Stevenson

[11] 4,427,827

[45] Jan. 24, 1984

[54] SYNTHESIS OF HORMONE FRAGMENTS

[75] Inventor: David Stevenson, Scarsdale, N.Y.

[73] Assignee: USV Pharmaceutical Corporation, Tarrytown, N.Y.

[21] Appl. No.: 435,581

[22] Filed: Oct. 20, 1982

[51] Int. Cl.³ .................... C07C 103/52; C08L 89/00
[52] U.S. Cl. ........................... 525/54.11; 260/112.5 R
[58] Field of Search ............... 260/112.5 R; 525/54.11

[56] References Cited

U.S. PATENT DOCUMENTS

| | | | |
|---|---|---|---|
| 3,891,614 | 6/1975 | Sakakibara et al. | 260/112.5 |
| 4,055,524 | 8/1977 | Colescott et al. | 260/8 |
| 4,105,602 | 8/1978 | Colescott et al. | 260/8 |

OTHER PUBLICATIONS

Stewart & Young, Solid Phase Peptide Synthesis, pp. 38–39 (W. H. Freeman, Publishers) 1st Edition, 1969.
Lenard et al., J. Am. Chem. Soc., 89:1, Jan. 4, 1967.

*Primary Examiner*—Delbert R. Phillips
*Assistant Examiner*—F. T. Moezie

[57] ABSTRACT

The yield of peptide synthesis processes of the type in which a protected intermediate resin peptide of the formula Resin—$CH_2$—O—Phe—X, Resin—$CH_2$—O—Gly—X, Resin—$CH_2$—O—Ala—X, or Resin—$CH_2$—O—Leu—X is deprotected, and successively protected amino acids are coupled to the resin peptide and deprotected, is increased significantly by deprotecting the first residue with trifluoroacetic acid and deprotecting the other residues with hydrogen chloride.

14 Claims, No Drawings

SYNTHESIS OF HORMONE FRAGMENTS

BACKGROUND OF THE INVENTION

This invention relates to the synthesis of peptides and in particular to solid-phase synthesis employing an insoluble resin. More specifically, the present invention provides peptide chains useful in the treatment of hormone deficiencies of the human body, such as human parathyroid hormone (hPTH), its amino-terminal 1–34 sequence, and analogs thereof, via an improved process which produces the peptide chains of interest in significantly higher yields.

U.S. Pat. No. 4,105,602 describes a solid-phase process for synthesizing hPTH using an insoluble polystyrene resin. The resin is chloromethylated at a number of sites to form a reactive resin product of the formula R—CH$_2$Cl where R is the resin. Phenylalanine having a protective group such as tertiarybutyloxycarbonyl (BOC), amyloxycarbonyl (AMOC) or orthonitrophenylsulfenyl (NPS) on the α-amino group is reacted with the resin to form R—CH$_2$—O—Phe—X where Phe is the phenylalanine residue and X is the amino-protecting group, and the phenylalanine residue is deprotected by removal of the amino-protecting group X. Successive amino acids, each having a suitable protecting group on the α-amino group, are coupled to the preceding amino acid residue on the growing resin-peptide chain by amide formation; each newly added amino acid is deprotected prior to addition of the next amino acid. When the desired peptide chain has been assembled, it is cleaved from the resin by reaction with HF.

In the aforementioned patent, trifluoroacetic acid (TFA) is illustrated exclusively as the reagent used to deprotect the phenylalanine and all other amino acid residues following attachment of the protected amino acids to the peptide chain. Indeed, TFA has for a number of years been a widely accepted reagent of choice for deprotection in all related peptide synthesis. The patent also mentions hydrochloric acid as a suitable deprotecting reagent, and hydrochloric acid in dioxane has been disclosed in a deprotecting process (Stewart & Young, Solid Phase Peptide Synthesis, 1st Ed., Freeman Pub. Co., 1969, pp. 38–39). Hydrochloric acid in glacial acetic acid is also disclosed in U.S. Pat. No. 3,891,614, as a deprotecting agent in the synthesis of calcitonin.

SUMMARY OF THE INVENTION

The invention comprises an improvement in the synthesis of a resin peptide of the formula R—CH$_2$—O—Z, from an intermediate resin peptide of the formula R—CH$_2$—O—Y—X wherein R is an insoluble polystyrene resin;
Y is a terminal amino acid residue selected from the group consisting of Phe, Gly, Leu and Ala;
X is a protecting group in the α-amino position of Y; and
Z is either
a fragment (n-m) of human parathyroid hormone or an analog thereof in which Y is Phe and m is 34; Y is Gly and m is 12; or Y is Leu and m is 7, 11, 15, 24, or 28; and n is an integer from 1 to (m minus 1); or
a fragment (n-m) of human calcitonin or an analog thereof in which Y is Phe and m is 5, 8, or 11; Y is Gly and m is 2, 10, 28, or 30; Y is Leu and m is 4 or 9; or Y is Ala and m is 26 or 31; and n is an integer from 1 to (m minus 1);
wherein the residue Y is deprotected and neutralized and in succession each of the other amino acids whose residues comprise the fragment Z, each having a protecting group in the α-amino position, is coupled to the next preceding residue on the resin peptide and then deprotected and neutralized, the improvement comprising (a) deprotecting the residue Y with trifluoroacetic acid, and
(b) deprotecting the other residues with hydrogen chloride dissolved in a solvent selected from the group consisting of dioxane and ethers containing from 4 to 6 carbon atoms.

DETAILED DESCRIPTION OF THE INVENTION

As indicated, the present invention is useful in the synthesis of resin peptides comprising a sequence of amino acid residues coupled at one end to an insoluble polystyrene resin. The conventional abbreviations for identifying amino acids and their residues (e.g., Phe=phenylalanine, etc.) will be employed herein, and it will be apparent from the context whether an abbreviation refers to an acid or its residue. The peptide chain can be cleaved from the resin peptide by known processes, e.g., cleavage from the resin with HF, and filtration from the resin, and then isolated and used in the preparation of biologically active compositions.

Insoluble resins useful herein are polymeric materials which are insoluble in but solvated and penetrated by the solvents used in peptide synthesis (e.g., methylene chloride, toluene, dioxane, and furans) and which are capable of providing an active receptor site for the first amino acid in the peptide chain of interest (e.g., Phe, Gly, Leu, or Ala). A preferred insoluble resin is a polystyrene resin obtained by the catalytic polymerization of styrene crosslinked with about 1 to 2% of divinyl benzene, or by the grafting of linear polystyrene to a core of trifluorochloroethylene. The selected resin is chloromethylated in known fashion (e.g., using chloromethylmethylether and stannic chloride catalyst) to form a reactive resin species R—CH$_2$Cl where R is the resin.

Prior to being coupled to the reactive resin, the phenylalanine, glycine, leucine or alanine is reacted with a protecting species X (BOC, preferably, or AMOC or NPS) in known fashion to form a residue having the formula

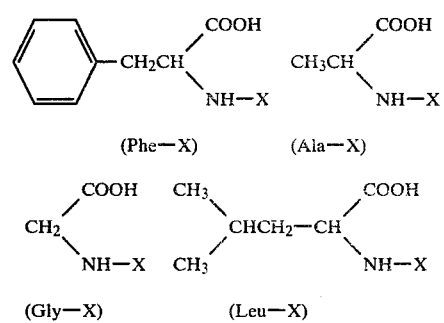

in which X protects the α-amino group.

The protected residue (hereinafter "Y—X") is then coupled to the resin in known fashion by the reactions Y—X+R—CH$_2$Cl R—CH$_2$—O—Y—X+HCl.

To assemble a resin peptide in accordance with the present invention, it is necessary first to deprotect the residue on the intermediate resin peptide R—CH$_2$—O—Y—X, that is, to remove the protecting group from the α-amino group on the Phe, Gly, Leu, or Ala residue. This step is carried out by reacting the intermediate resin peptide with an effective amount (at least stoichiometric based on the amount of protecting group) of trifluoroacetic acid (TFA) in a solvent for the TFA, under conditions of time (10-60 min.) and temperature (10°-20° C.) effective to permit removal of the protecting group from the alpha-nitrogen. The reaction mixture is subsequently neutralized with a base. It is, of course, highly desirable that deprotection be complete. This step is illustrated in the following example.

EXAMPLE 1

A 10.4 g. sample of BOC-L-phenylalanine resin (polystyrene cross-linked with 1% divinyl benzene) (coresponding to 8.0 mmoles phenylalanine) was placed in the reactor vessel of a Vega Model 50 automated peptide synthesizer (Vega Biochemicals, P.O. Box 11648, Tucson, AZ 85734). The resin was swollen by shaking for five minutes with 200 ml. toluene and then was washed four times, each for one minute, with 100 ml. portions of toluene. The resin was next washed for one minute with a solution consisting of 60 ml. toluene plus 60 ml. redistilled trifluoroacetic acid, and then permitted to react for thirty minutes with 120 ml. of 50% v/v/ trifluoroacetic acid in toluene. After draining the resin, it was washed, each for one minute, with three 100 ml. portions of toluene and then with six 100 ml. portions of 15% v/v methanol in toluene. The resin was neutralized by treating, once for one minute and once for three minutes with two 150 ml. portions consisting of five parts di-isopropylamine, ten parts methanol and eighty-five parts toluene (all v/v). Further washes were performed, for one minute each, with three 100 ml. portions of 15% v/v methanol in toluene and three 100 ml. portions of methylene chloride. Total neutralization was ensured by treating for two minutes with 150 ml. of 5% v/v di-isopropylamine in methylene chloride followed by washes each for one minute with six 100 ml. portions of methylene chloride. A ninhydrin test (Kaiser, et al., Anal. Biochem. 34, 595-8, 1969) was positive, as it should be if deprotection was complete.

To confirm that deprotection was complete, a small sample of the resin (50 mg) was acetylated by shaking for fifteen minutes with 10 ml. of a solution consisting of 5 ml. acetic anhydride, 5 ml. pyridine and 50 ml. methylene chloride. This was washed with methanol (2×10 ml.) and methylene chloride (4×10 ml.) and a ninhydrin test performed on a portion of the resin. The remainder of the acetylated resin was treated with 10 ml. of 50% v/v trifluoroacetic acid in toluene for fifteen minutes, washed with 10 ml. portions of toluene (three), methanol (three), 5% di-isopropylamine in methylene chloride (one), methylene chloride (six) and a ninhydrin test performed on part of this resulting resin. Both ninhydrin tests were negative when deprotection was complete.

The synthesis of the desired resin peptide continues by coupling the next amino acid, also having a protecting group on the α-amino group, to the deprotected intermediate resin peptide R—CH$_2$—O—Phe, R—CH$_2$—O—Gly, R—CH$_2$—O—Leu, or R—CH$_2$—O—Ala. Any of a number of suitably protected amino acids can be coupled to the intermediate resin peptide. Example 2 describes the coupling of BOC-asparagine (protected), which is the next amino acid in the sequence leading to human parathyroid hormone fragment (1-34).

EXAMPLE 2

To the deprotected L-phenylalanine resin, with 8 meq of amine groups, was added the acylating solution, containing 24 mmoles N (α)—BOC—L-asparagine. This acylating solution was preared by dissolving 5.6 g. BOC-asparagine, prepared previously from L-asparagine in known fashion, in 12 ml. dimethylformamide, plus 28 ml. of M 1-hydroxybenzotriazole in dimethylformamide; to this solution was added toluene, 40 ml., and the resulting solution was cooled to 0°-5° C.; 12 ml. 2 M N,N'-dicyclohexylcarbodiimide in toluene was added and the solution was stirred for thirty minutes at room temperature, during which time a precipitate of dicyclohexylurea separated. This precipitate was filtered off, washed with 40 ml. toluene, and the acylating solution resulting from the combined filtrate and washings was added to the resin. The mixture was shaken for about 24 hours. The resin was drained and washed for one minute each time with three 100 ml. portions of toluene, six 100 ml. portions of methanol, six 100 ml. portions of methylene chloride and three 100 ml. portions of toluene. Coupling should be allowed to proceed at least overnight to ensure that the reaction proceeds to completion. A ninhydrin test was performed to confirm that complete coupling had occurred.

Following coupling, the protecting group is removed from the amino acid, and the peptide chain is assembled by successively coupling to the deprotected resin peptide an amino acid protected in the α-amino position, removing the protecting group, and then neutralizing. In a novel aspect of the present invention, the amino acids added to the resin peptide after deprotection of the initial Phe, Gly, Leu, or Ala residue adjacent to the resin are deprotected with hydrogen chloride, notwithstanding the fact that the initial residue is deprotected with trifluoroacetic acid. Deprotecting the residues in this manner produces the desired resin peptide in significantly higher yield compared to employing TFA to deprotect all the residues as is conventional practice, or compared to employing HCl for all deprotection steps including deprotection of the initial residue with HCl. The improvement in the yield of products in which Leu is the initial residue, while not as pronounced, is still significant, and the yield itself is quite high (i.e., over 90%). The yields of peptide chains produced by the invention can be 40% and higher.

Deprotecting with HCl should be carried out in a solvent in which HCl and the removed protecting group, but not the resin peptide, are soluble. Advantageously, the concentration of HCl is about 2 N to about 6 N, and more advantageously about 3.5 N to about 4.0 N. Suitable solvents include dioxane, and saturated and unsaturated cyclic or straight-chain ethers, preferably ethers having 4 to 6 carbon atons, such as tetrahydrofuran or diethyl ether. Acetic acid is not recommended because it can cause unacceptable acetylation of the peptide chain. The deprotecting solution also preferably contains a thiol, such as 2-mercaptoethanol, in an amount (usually about 1 to about 2 vol. %) effective to inhibit attack by the removed protecting group (e.g., t-butylcarbonium ion) on the resin peptide chain. The protected resin peptide is washed again and neutralized with e.g. a secondary amine that does not react with the resin peptide.

The improvement comprising the present invention is useful in the preparation of all or a portion of human parathyroid hormone fragment (1-34), in which the product ends with a Phe, Gly, or Leu residue. According to conventional terminology hPTH has the structure Ser—Val—Ser—Glu—Ile—Gln—Leu—Met—His—Asn—
1                             5                                  10

Leu—Gly—Lys—His—Leu—Asn—Ser—Met—Glu—Arg—
11                             15                                 20

Val—Glu—Trp—Leu—Arg—Lys—Lys—Leu—Gln—Asp—
21                             25                                 30

Val—His—Asn—Phe—
31                      34

The product made herein when Phe is the initial residue, adjacent to the resin, comprises hPTH fragment (n-34) where n is an integer from 1 to 33; e.g., where n is 1, the product is the fragment (1-34). When Gly is the initial residue, the product made herein is the hPTH fragment (n-12) where n is an integer from 1 to 11, such as hPTH fragment (5-12). Any Leu-terminal fragment (n-m) can also be made to advantage using this invention; since Leu occurs at five sites on the hPTH (1-34) chain, m can be 7, 11, 15, 24, or 28 (corresponding to the location of Leu on the chain) and n can be an integer from 1 to (m minus 1), e.g., hPTH (1-7), hPTH (1-11), hPTH (18-24), hPTH (13-24), and so on. The Leu-terminal and Gly-terminal fragments are useful in the synthesis of hPTH (1-34) by routes involving the coupling of previously assembled intermediate fragments.

The fragment (n-34) is produced from the resin peptide R—CH$_2$—O—Phe—X by deprotecting the Phe residue with TFA, and then coupling the appropriate successive amino acids and deprotecting them with HCl as described herein. The fragment (n-12) is produced by deprotecting the resin peptide R—CH$_2$—O—Gly—X with TFA, and then coupling the other acids and deprotecting them with HCl.

The improvement of this invention is also useful in the preparation of any portion of human calcitonin (hCT) or analogs thereof having a terminal Phe, Gly, Leu or Ala residue. Human calcitonin has the structure

```
   ┌─────────────────────────────┐
H—Cys—Gly—Asn—Leu—Ser—Thr—Cys—
   1                   5
```

—Gly—Thr—Tyr—Thr—Gln—Asp—Phe—Asn—Lys—Phe—
10                                15

—His—Thr—Phe—Pro—Gln—Thr—Ala—Ile—Gly—Val—
20                                25

—Gly—Ala—Pro—NH$_2$
30 and can be synthesized in a manner wholly analogous to the method described herein for hPTH. In other words, a fragment of hCT can be synthesized by a conventional sequence starting from a resin peptide Resin—CH$_2$—O—Phe—X, Resin—CH$_2$—O—Gly—X, Resin—CH$_2$—O—Leu—X, or Resin—CH$_2$—O—Ala—X, where the resin is as described above, deprotecting the initial amino acid residue with TFA, and then deprotecting all subsequently coupled protected amino acids with HCl.

The present invention significantly increases the formation of resin peptides of the desired length, and significantly increases the percentage of those resin peptides formed which have the desired sequence of amino acids. Preferably, the advantages of this discovery are realized by deprotecting all the residues following the initial Phe, Gly, Leu or Ala with HCl; it will be recognized that the advantages can be realized by deprotecting at least about 90%, or even at least about 75%, of the residues with HCl and deprotecting the remainder with TFA, but such additional interchange of the deprotecting reagent makes the overall process more cumbersome and sacrifices some of the improvement in the yield.

The preferred protecting group for the α-amino group on each amino acid is t-butyloxycarbonyl (BOC). Several acids have other groups which are also protected before coupling. The groups and the preferred protecting groups are as follows:

TABLE 1

| Protected Group | Protecting Group |
|---|---|
| ε-amino (in Lys) | trifluoroacetyl |
| imidazole N (in His) | benzyloxycarbonyl |
| guanidine N (in Arg) | tosyl |
| hydroxyl (in Ser) | benzyl |
| indole N (in Trp) | formyl |

It will be recognized that the protecting groups listed in the Table 1 need not be removed during the sequential coupling reactions. Coupling of each amino acid is carried out by conventional procedures known in the art and exemplified below. For instance, a stoichiometric excess of the protected amino acid and a like amount of a coupling agent such as dicyclohexylcarbodiimide are combined with the resin peptide, in e.g. methylene chloride, and allowed to react. The mixture is analyzed to determine whether coupling is complete. If it is not, recoupling is performed as is well known in the art.

In the synthesis of a fragment of hPTH of hCT which includes the His residue, it is advantageous following the coupling of the protected His acid and each subsequent acid, and before deprotection thereof, to include a base wash step to remove any labile acylating groups attached to the imidazole nitrogen on the His residue. For instance, the resin peptide can be washed for 5 minutes with a solution of a secondary amine, such as 5:10:85 vol. % di-isopropylamine:methanol:methylene chloride solution.

The use of HCl to deprotect a resin peptide is described in Example 3, and the preparation of human parathyroid fragment (1-34) incorporating the deprotection process of the present invention is described in Example 4. It will be evident that the synthesis described in Example 4 can be interrupted at any point to provide a resin peptide fragment (n-34), from which the peptide can be cleaved by conventional HF treatment. It will also be evident that the steps described in Example 4 to add the residues to the resin peptide can be employed as effectively when the Gly (12) residue or any of the Leu residues is attached to the resin as the initial residue. For instance, resin peptide fragments (28–34), (24–34), (18–24), (13–24), (5–12), (4–12), (1–15), (7–15), or any other desired fragment can be produced.

EXAMPLE 3

The resin peptide R—CH$_2$—O—Phe—Asn—X prepared in Example 2, where X is a BOC group on the α-amino group of the asparagine residue, was first washed, each for one minute, with three 100 ml. portions of dioxane containing 2% v/v 2-mercaptoethanol. It was then washed for one minute with 150 ml. 3.5–4.0 N HCl in dioxane containing 2% v/v 2-mercaptoethanol and permitted to react for thirty minutes with 150 ml. of the same solution. After draining, the resin was washed, each for one minute, with six 100 ml. portions of dioxane containing 2% v/v 2-mercaptoethanol and with three 100 ml. portions of methylene chloride. The resin was neutralized by treating, once for one minute and once for two minutes with two 150 ml. portions of 5% v/v diisopropylamine in methylene chloride. Further washes were performed, for one minute each, with three 100 ml. portions of methylene chloride. Total neutralization was ensured by treating for one minute with 150 ml. 5% v/v di-isopropylamine in methylene chloride, followed by washes, each for one minute, with six 100 ml. portions of methylene chloride. A ninhydrin test was positive.

EXAMPLE 4

To the deprotected dipeptide resin from Example 3, after incorporation of residue 33, was added the acylating solution, containing 24 mmoles N (α)-BOC, N(im)-Z-L-histidine. This acylating solution was prepared by dissolving 11.2 g. N(α)-BOC, N(im)-Z-histidine, containing one molecule of benzene of crystallization per molecule of protected amino-acid, in 100 ml. methylene chloride and cooling the resulting solution to 0°–5° C.; to this was introduced 12 ml. 2 M N,N'-dicyclohexylcarbodi-imide in toluene and the resulting mixture was added immediately to the resin peptide. The mixture was shaken for 1–3 hours, the resin drained and washed successively with three 100 ml. portions of methylene chloride for one minute each time, with one 150 ml. portion consisting of 5:10:85 v/v di-isopropylamine-methanol-methylene chloride with six 100 ml. portions of methanol for one minute each time and with six 100 ml. portions of methylene chloride for one minute each time. A ninhydrin test was then performed; it should be negative. The resulting resin peptide R—CH$_2$—O—Phe—Asn—His—BOC was deprotected exactly as described in Example 3.

Residues 31, 30 and 29 (Val. Asp. and Glu, respectively) each protected by a BOC group on the α-amino group, were then added to the resin peptide and deprotected. Each acid, in turn, was added as a solution containing 24 mmoles of BOC-(acid dissolved in 12 ml. dimethylformamide; to this solution was added 40 ml. methylene chloride, and the resulting solution was cooled to 0°–5° C.; 12 Ml. 2 M N,N'-dicyclohexylcarbodiimide in toluene was added and the solution was stirred for thirty minutes at room temperature, during which time a precipitate of dicyclohexylurea separated. This precipitate was filtered off and washed with 40 ml. methylene chloride, and the acylating solution resulting from the combined filtrate and washings was added to the resin. The mixture was shaken overnight. The resin was drained and washed for one minute each time with three 100 ml. portions of methylene chloride, one 150 ml. portion of 5:10:85 vol. % di-isopropylamine:methanol:methylene chloride, with six 100 ml. portions of methanol for one minute each, and with six 100 ml. portions of methylene chloride for one minute each. A ninhydrin test was negative.

Deprotection of the protected resin peptides R—CH$_2$—O—Phe—Asn—His—Val—BOC, R—CH$_2$—O—Phe—Asn—His—Val—Asp—BOC, and R—CH$_2$—O—Phe—Asn—His—Val—Asp—Glu—BOC, was performed exactly as described in Example 3.

To the deprotected hexapeptide resin, after washing for one minute each with three 100 ml. portions of dimethylformamide, was added the next acylating solution, containing 24 mmoles of BOC-L-leucine. This acylating solution was prepared by dissolving 6.0 g. (24 mmoles) BOC-L-leucine monohydrate in 100 ml. dimethylformamide and cooling the resulting solution to 0°–5° C.; to this was added 12 ml. of 2 M N,N-dicyclohexylcarbodi-imide in toluene, (24 mmoles DCC) and the resulting mixture was stirred for thirty minutes at room temperature. The precipitate of dicyclohexylurea, which separated was filtered off and washed with dimethylformamide (40 ml.), and the acylating solution resulting from the combined filtrate and washings was added to the resin. The mixture was shaken overnight. The resin was drained and washed for one minute each time with three 100 ml. portions of dimethylformamide, with one 150 ml. portion consisting of 5:10:85 v/v di-isopropylamine-methanol-methylene chloride, with six 100 ml. portions of methanol for one minute each time, and with six 100 ml. portions of methylene chloride for one minute each time. A ninhydrin test was performed and was negative. Deprotection of the resin was performed exactly as described in Example 3, thereby providing a resin peptide having the structure R—CH$_2$—O—Phe—Asn—His—Val—Asp—Glu—Leu.

Amino acids 27 through 1, except for His (9) and His (14), were each coupled and deprotected using the procedure described for the coupling and deprotection of Leu (28). The His (9 and 14) was coupled and deprotected by the procedure described for coupling His (32), except that the washing cycles were the same as those described for Leu (28).

The resulting resin peptide in which the peptide chain corresponds to human parathyroid hormone fragment (1–34), can be cleaved from the resin with HF, and recovered by known techniques.

EXAMPLE 5

For purposes of comparison, the preparation of human parathyroid hormone fragment (1–34) was attempted in two tests which were identical except as to the manner of deprotection. In one test, a 50 vol. % solution of TFA in toluene was employed as the deprotecting agent in all deprotection steps, and in the other sample the initial Phe residue on the resin peptide was deprotected with 50 vol. % TFA in toluene and all other residues were deprotected using a 3.5–4.0 N solution of HCl in dioxane containing 2 vol. % 2-mercaptoethanol.

Each test started with 10 g. of BOC—Phe—resin, substituted with 0.8 meq Phe/g. The resin was the same resin used in Examples 3–4. After addition and deprotection of the remaining 33 amino acids the amount of final resin peptide was weighed. This product was then cleaved with HF, treated with an aqueous piperidine solution containing 2 vol. % 2-mercaptoethanol, and the resin was filtered off; the peptide chain was recovered and analyzed by high-pressure liquid chromatography to determine the hPTH content of the peptide chain. The results were:

TABLE 2

|  | Deprotection Method | |
| --- | --- | --- |
|  | TFA Throughout | TFA for Phe, HCl Thereafter |
| Weight increase of resin peptide | | |
| Amount | 26 g | 37 g |
| As % of theoretical | 59% | 84% |
| Amount of hpTH (1-34) in cleaved peptide as % of total peptide | 38% | 50% |
| Yield of hpTH (1-34) As % of theoretical | 22% | 42% |

The improvement from 59% to 84% in the weight increase of the resin peptide indicates that deprotection according to the process of the present invention promotes greater formation of peptide chains on the resin. The improvement from 38% to 50% in the amount of hPTH (1-34) in the cleaved peptides indicates that the present invention also promotes greater specificity, i.e., more of the peptide chains that form correspond in structure to hPTH (1-34). Both of these improvements are significant in themselves, and lead to the even more significant improvement from 22% to 42% in the yield of hPTH (1-34) by the overall process. Thus, in this example the overall yield nearly doubles. This result is quite significant and is not expected from previously reported peptide synthesis and deprotection processes.

What is claimed is:

1. In the synthesis of a resin peptide of the formula R—$CH_2$—O—Z, from an intermediate resin peptide of the formula R—$CH_2$—O—Y—X wherein R is an insoluble polystyrene resin;

Y is a terminal amino acid residue selected from the group consisting of Phe, Gly, Leu and Ala;

X is a protecting group in the α-amino position of Y; and

Z is either a fragment (n-m) of human parathyroid hormone or an analog thereof in which Y is Phe and m is 34; Y is Gly and m is 12; or Y is Leu and m is 7, 11, 15, 24, or 28; and n is an integer from 1 to (m minus 1); or a fragment (n-m) of human calcitonin or an analog thereof in which Y is Phe and m is 5, 6, or 11; Y is Gly and m is 2, 10, 28, or 30; Y is Leu and m is 4 or 9; or Y is Ala and m is 26 or 31; and n is an integer from 1 to (m minus 1);

wherein the residue Y is deprotected and neutralized and in succession each of the other amino acids whose residues comprise the fragment Z, each having a protecting group in the α-amino position, is coupled to the next preceding residue on the resin peptide and then deprotected and neutralized, the improvement comprising (a) deprotecting the residue Y with trifluoroacetic acid, and (b) deprotecting the other residues with hydrogen chloride dissolved in a solvent selected from the group consisting of dioxane and ethers containing from 4 to 6 carbon atoms.

2. In the synthesis of a resin peptide of the formula R—$CH_2$—O—Z, from an intermediate resin peptide of the formula R—$CH_2$—O—Y—X wherein R is an insoluble polystyrene resin;

Y is a terminal amino acid residue selected from the group consisting of Phe, Gly, and Leu;

X is a protecting group in the α-amino position of Y; and

Z is a fragment (n-m) of human parathyroid hormone or an analog thereof in which Y is Phe and m is 34; Y is Gly and m is 12; or Y is Leu and m is 7, 11, 15, 24, or 28; and n is an integer from 1 to (m minus 1);

wherein the residue Y is deprotected and neutralized and in succession each of the other amino acids whose residues comprise the fragment Z, each having a protecting group in the α-amino position, is coupled to the next preceding residue on the resin peptide and then deprotected and neutralized, the improvement comprising (a) deprotecting the residue Y with trifluoroacetic acid, and (b) deprotecting the other residues with hydrogen chloride dissolved in a solvent selected from the group consisting of dioxane and ethers containing from 4 to 6 carbon atoms.

3. The process of claim 1 wherein the hydrogen chloride has a concentration of about 3.5 N to about 4.0 N and the solvent is dioxane.

4. The process of claim 3 wherein the hydrogen chloride solution also contains about 1 vol. % to about 2 vol. % of a thiol.

5. The process of claim 4 wherein the thiol is 2-mercaptoethanol.

6. The process of claim 1 wherein the protecting group removed in each deprotecting step is t-butyloxycarbonyl.

7. The process of claim 1 wherein the trifluoroacetic acid is dissolved in toluene, methylene chloride, or a mixture thereof.

8. The process of claim 1 wherein n is 1.

9. The process of claim 1 wherein Z is a fragment (28-34) of human parathyroid hormone, and Y is Phe.

10. The process of claim 1 wherein Z is a fragment (5-12) of human parathyroid hormone, and Y is Gly.

11. The process of claim 1 wherein Z is a human parathyroid hormone fragment, Y is Leu, m is 7, 11, 15, 24, or 28, and n is (m minus 6).

12. The process of claim 9 wherein the hydrogen chloride has a concentration of about 3.5 N to about 4.0 N and the solvent is dioxane.

13. The process of claim 10 wherein the hydrogen chloride has a concentration of about 3.5 N to about 4.0 N and the solvent is dioxane.

14. The process of claim 11 wherein the hydrogen chloride has a concentration of about 3.5 N to about 4.0 N and the solvent is dioxane.

* * * * *